(12) United States Patent
Olivier et al.

(10) Patent No.: US 6,716,350 B2
(45) Date of Patent: Apr. 6, 2004

(54) MICROPLATE PROTECTIVE TRAY UNDERCOVER

(75) Inventors: Stephane Olivier, Rosheim (FR); Alan J. Weiss, Acton, MA (US)

(73) Assignee: Millipore Corporation, Bedford, MA (US)

( * ) Notice: Subject to any disclaimer, the term of this patent is extended or adjusted under 35 U.S.C. 154(b) by 0 days.

(21) Appl. No.: 10/138,597

(22) Filed: May 3, 2002

(65) Prior Publication Data

US 2003/0205511 A1 Nov. 6, 2003

(51) Int. Cl.$^7$ ............................................... B01D 63/00
(52) U.S. Cl. ............................ 210/321.6; 210/321.61; 210/321.75; 210/321.84; 210/323.1; 422/58; 422/101; 422/104; 250/328
(58) Field of Search ........................ 210/321.6, 321.61, 210/321.75, 321.84, 323.1, 483; 422/101, 104, 58, 48; 250/328; 436/177, 809

(56) References Cited

U.S. PATENT DOCUMENTS

| | | | |
|---|---|---|---|
| 4,493,815 A | * 1/1985 | Fernwood et al. | 422/101 |
| 4,526,690 A | 7/1985 | Kiovsky et al. | 210/335 |
| 4,704,255 A | 11/1987 | Jolley | 422/101 |
| 4,734,192 A | 3/1988 | Champion et al. | 210/335 |
| 4,777,021 A | 10/1988 | Wertz et al. | 422/101 |
| 4,797,259 A | 1/1989 | Matkovich et al. | 422/101 |
| 4,833,087 A | 5/1989 | Hinckley | 435/287 |
| 5,294,795 A | * 3/1994 | Lehtinen et al. | 250/328 |
| 5,460,783 A | 10/1995 | Hautea et al. | 422/104 |
| 5,779,907 A | 7/1998 | Yu | 210/695 |
| 5,885,499 A | 3/1999 | Aksberg | 264/153 |
| 5,961,926 A | 10/1999 | Kolb et al. | 422/101 |
| 6,514,464 B1 | * 2/2003 | Knebel | 422/102 |

FOREIGN PATENT DOCUMENTS

| | | |
|---|---|---|
| WO | 98/14277 | 4/1998 |
| WO | 01/92461 | 12/2001 |

* cited by examiner

*Primary Examiner*—Joseph Drodge
*Assistant Examiner*—K S Menon
(74) *Attorney, Agent, or Firm*—Nields & Lemack

(57) ABSTRACT

A laboratory device design particularly for a multiplate format that includes a tray having at least one well with a support associated with the well, and a removable undercover. The undercover protects the support or membrane from external contamination without causing excessive force on an individual well that can cause membrane flatness. The undercover is easily removable to provide access to the support or membrane. The undercover, when affixed to the underside of the multiwell plate or tray, allows the assembly to be transportable as a single unit while still being in compliance with SBS automation standards.

12 Claims, 8 Drawing Sheets

MICROPLATE PROTECTIVE TRAY UNDERCOVER

BACKGROUND OF THE INVENTION

Test plates for chemical or biochemical analyses, which contain a plurality of individual wells or reaction chambers, are well-known laboratory tools. Such devices have been employed for a broad variety of purposes and assays, and are illustrated in U.S. Pat. Nos. 4,734,192 and 5,009,780, for example. Microporous membrane filters and filtration devices containing the same have become particularly useful with many of the recently developed cell and tissue culture techniques and assays, especially in the fields of virology and immunology. Multiwell plates, used in assays, often utilize a vacuum applied to the underside of the membrane as the driving force to generate fluid flow through the membrane. The microplate format has been used as a convenient format for plate processing such as pipetting, washing, shaking, detecting, storing, etc.

Typically, a 96-well filtration plate is used to conduct multiple assays simultaneously. In the case of multiwell products, a membrane is placed on the bottom of each of the wells. The membrane has specific properties selected to filter or to support biological or chemical reactions. High throughput applications, such as DNA sequencing, PCR product cleanup, plasmid preparation, drug screening and sample binding and elution require products that perform consistently and effectively.

One such filtration device commercially available from Millipore Corporation under the name "Multiscreen" is a 96-well filter plate that can be loaded with adsorptive materials, filter materials or particles. The Multiscreen underdrain has a phobic spray applied in order to facilitate the release of droplets. More specifically, the MultiScreen includes an underdrain system that includes a spout for filtrate collection. This spout not only directs the droplets but also controls the size of the droplets. Without the underdrain system, very large drops form across the entire underside of the membrane and can cause contamination of individual wells. Access to the membrane can be had by removing the underdrain. However, assay results are sensitive to liquid collection between the membrane and the underdrain due to membrane weeping. Also, membrane flatness can be problematic depending on the reading technology used. The device also is not compatible with automated robotics equipment such as liquid handlers, stackers, grippers and bar code readers.

A conventional application for the microplate format that does not involve filtration is enzyme linked immuno-spot (ELISPOT) assays. In an ELISPOT assay, for example, the wells of the ELISPOT plate are coated with an antibody that is specific for the cytokine that is being assayed for. The antibody binds to the nitrocellulose or polyvinylidene fluoride (PVDF) membrane portion of the ELISPOT plate. Activated peripheral mononuclear cells are transferred to the plate, and the cytokines are released during an incubation period. The released cytokines bind to and are therefore captured by the specific antibody. The cells and excess cytokines are washed away, and a second antibody also specific for the cytokine of interest that is coupled to an enzyme capable of converting a substrate into an insoluble colored product is added. The substrate is converted into an insoluble product, forming spots or colors that represent the areas of captured cytokines. The spots can be quantitated using a microscope or digital imaging system. The ELISPOT assay provides an effective method of measuring antibody or cytokine production of immune cells on the single cell level.

In applications such as ELISPOT assays where the membrane is not used as a filter, but rather as a substrate upon which a biochemical reaction occurs and is detected, the underdrain not only becomes unnecessary, but also can be problematic. The underdrain both hinders access to the membrane for imaging and can cause the membrane to bow, which also deleteriously effects imaging. In addition, leakage or weeping of liquid through the membrane into the area between the membrane and the underdrain can ruin the assay, and may be dangerous to the user if the samples or reagents involved are biohazards, for example.

The Society for Biomolecular Screening (SBS) has published certain dimensional standards for microplates in response to non-uniform commercial products. Specifically, the dimensions of microplates produced by different vendors varied, causing numerous problems when microplates were to be used in automated laboratory instrumentation. The SBS standards address these variances by providing dimensional limits for microplates intended for automation.

It would therefore be desirable to provide a multiplate format that allows for easy access to the membrane while reducing or eliminating the deleterious retention of liquid under the membrane, loss of membrane flatness, and/or accidental separation of the wells from the tray.

It also would be desirable to provide a multiplate format that is automation compatible.

SUMMARY OF THE INVENTION

The problems of the prior art have been overcome by the present invention, which provides a laboratory device design particularly for a multiplate format that includes a plate or tray having at least one well with a support associated with the well, and a removable undercover. The undercover protects the support or membrane from external contamination without causing excessive force on an individual well that can interfere with the membrane's flatness. The undercover is easily removable to provide access to the support or membrane.

According to a preferred embodiment of the present invention, there is provided a multiwell device including a multiwell plate or tray having a membrane as a support, and an undercover affixed to the underside of the multiwell plate or tray so that the plate or tray and undercover are transportable as a single unit, the undercover being removable from the plate or tray, the multiwell device meeting SBS automation standards even with the undercover in place.

DETAILED DESCRIPTION OF THE INVENTION

Figure 1:
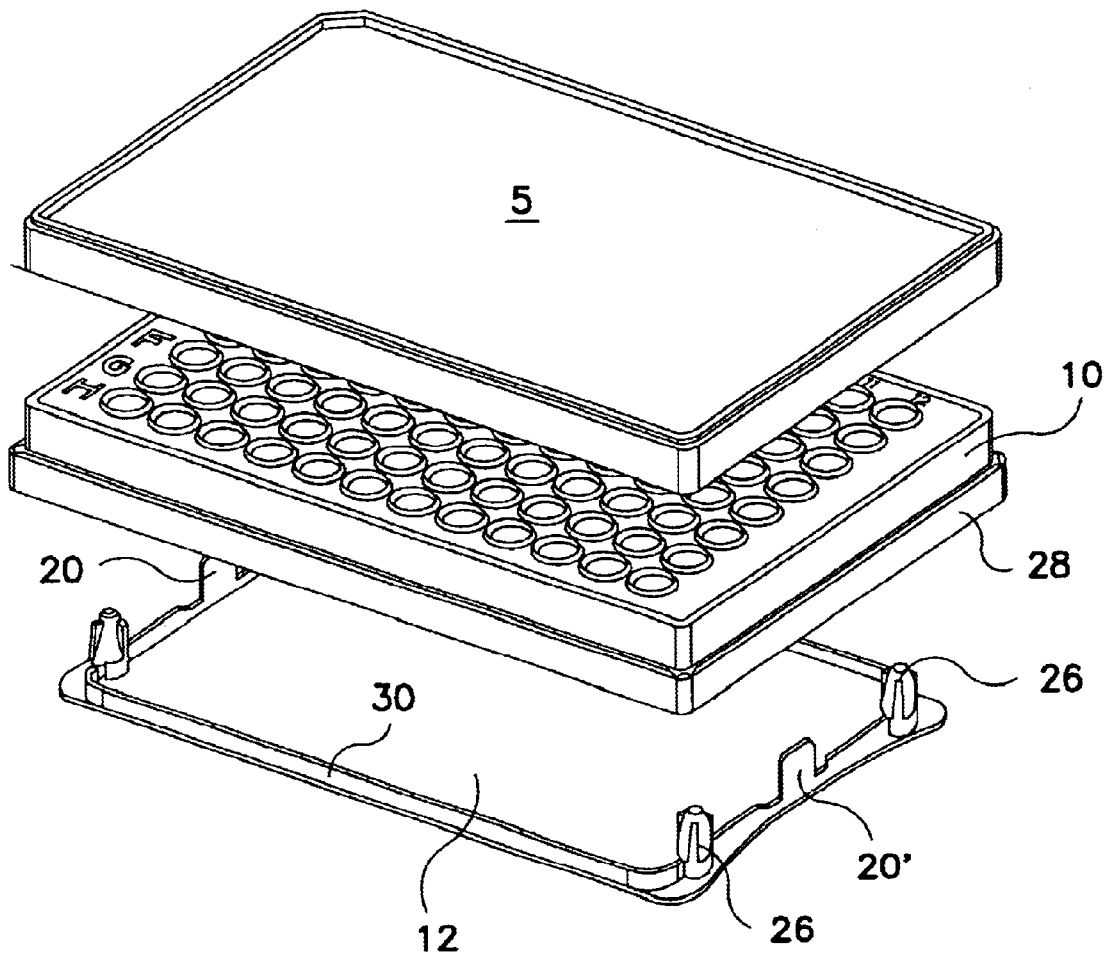
FIG. 1 is an exploded perspective view of a multiwell microplate device and undercover in accordance with the present invention.

Turning first to FIG. 1, there is shown a multiwell device including an optional removable protective cover 5, a 96-well plate or tray 10 and an undercover 12. Although a 96-well plate array is illustrated, those skilled in the art will appreciate that the number of wells is not limited to 96; a single well could be used, or standard multiwell formats with 384, 1536 or fewer or more wells are within the scope of the present invention. The well or wells are preferably cylindrical with fluid-impermeable walls, and have a width and depth according to the desired use and amount of contents to be sampled. Where a plurality of wells is present, the wells are preferably interconnected and arranged in a uniform array, with uniform depths so that the tops and bottoms of the wells are planar. The plate 10 is generally rectangular, although other shapes are within the scope of the present invention, keeping in mind the objective of meeting SBS dimensional standards.

Figure 5:
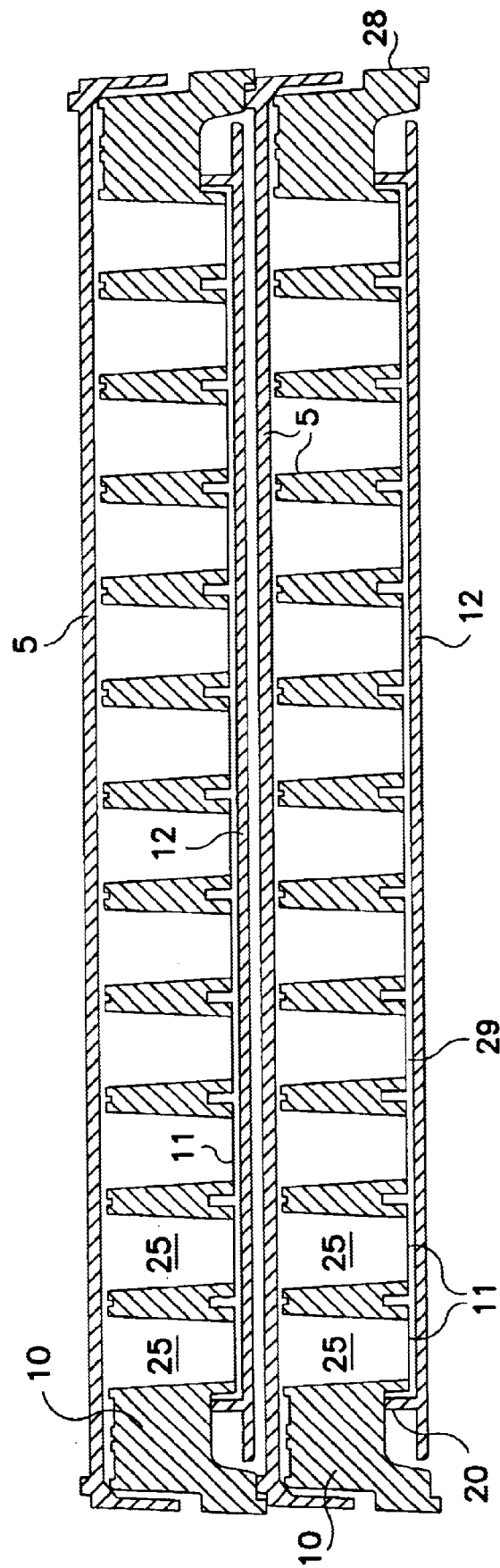
FIG. 5 is a cross-sectional view showing two stacked microplates with undercovers attached in accordance with an embodiment of the present invention.
Figure 8:
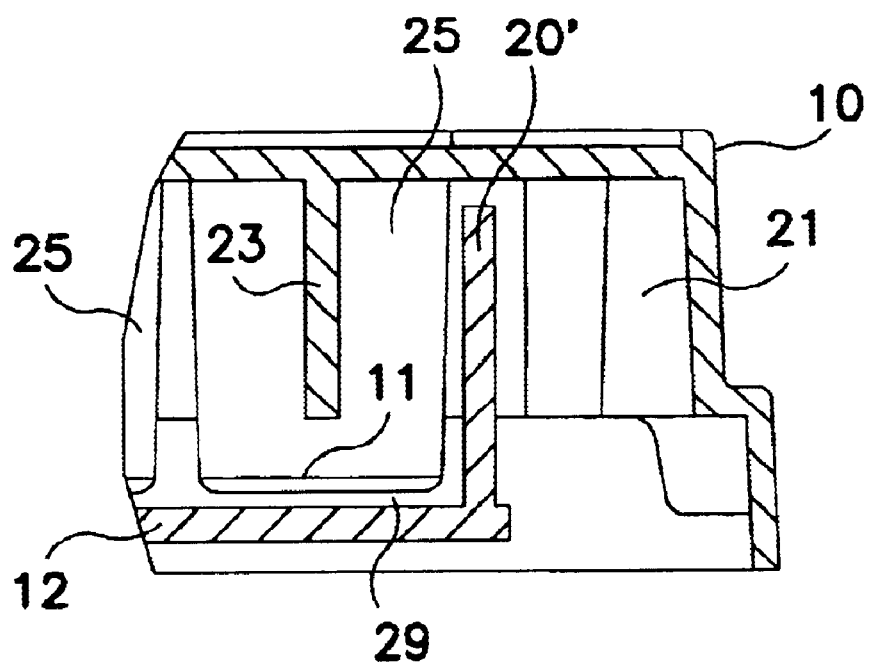
FIG. 8 is a cross-sectional view of a portion of the microplate with the undercover in place in accordance with the present invention.

In the embodiment shown, the plate 10 includes a plurality of wells having an open top and a bottom having a surface to which is sealed a substrate or support 11, such as a membrane (FIGS. 5 and 8). The sealing can be accomplished by any suitable means, including heat-sealing, sealing with ultrasonics, solvents, adhesives, by diffusion bonding, etc. The type of membrane suitable is not particularly limited, and can include nitrocellulose, cellulose acetate, polycarbonate, polypropylene and PVDF microporous membranes, or ultrafiltration membranes such as those made from polysulfone, PVDF, cellulose or the like. A single support covering all of the wells could be used, or where the device is a plurality of wells, each well can contain or be associated with its own support which can be the same or different from the support associated with one or more of the other wells. Each such individual support is preferably coextensive with the bottom of its respective well.

Depending on the anticipated mode of assay analysis, the undercover 12 may or may not be made of material sufficiently transparent so as not to interfere with optical imaging processes. It might also be desirable for the material to retain its optical properties through the procedure or assay, including sterilization. For example, some materials tend to yellow with gamma radiation, deleteriously affecting subsequent imaging processes. Suitable materials that have been found to have acceptable optical properties and that retain their optical properties include acrylic, EASTAR polyester copolymer, polystyrene, polycarbonate, polyethylene, polypropylene, cyclic olefin polymer such as ZEONEX and ZEONOR, cyclic olefin copolymer such as TOPAS, and NAS, a copolymer of 70% polystyrene and 30% acrylic. Acrylic is particularly preferred. However, it is within the scope of the present invention to use opaque undercovers where optical imaging is not a concern.

Figure 2:
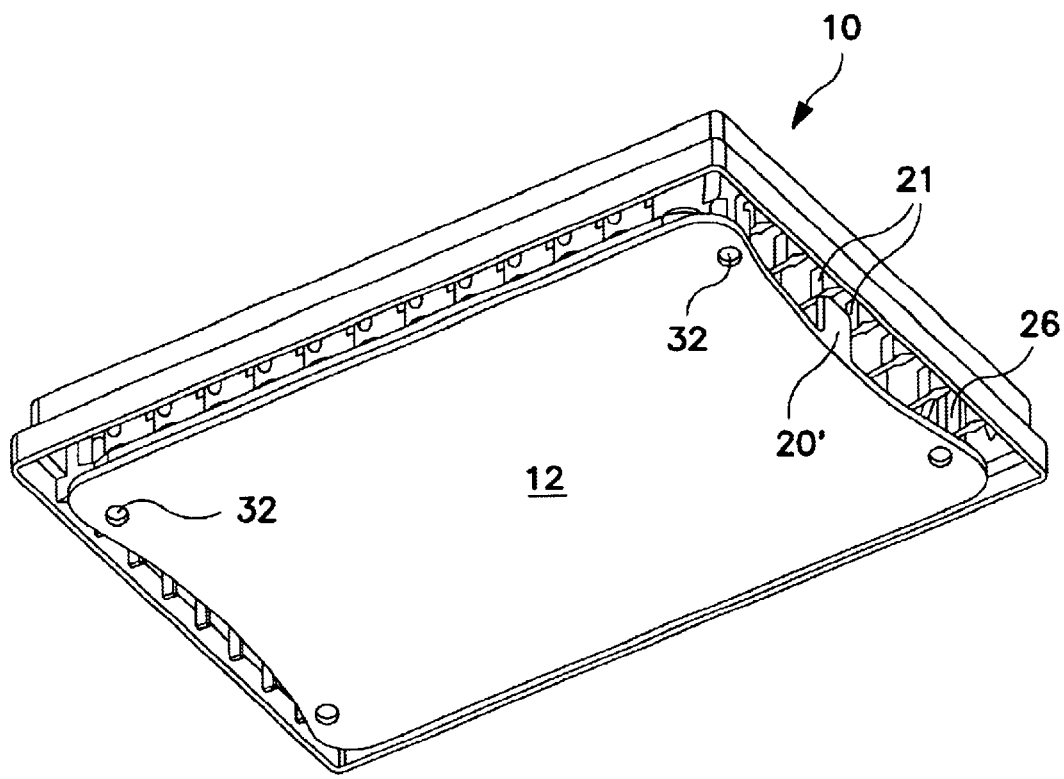
FIG. 2 is a perspective view showing the underside of a multiwell microplate device with the undercover affixed in place in accordance with the present invention.
Figure 3:
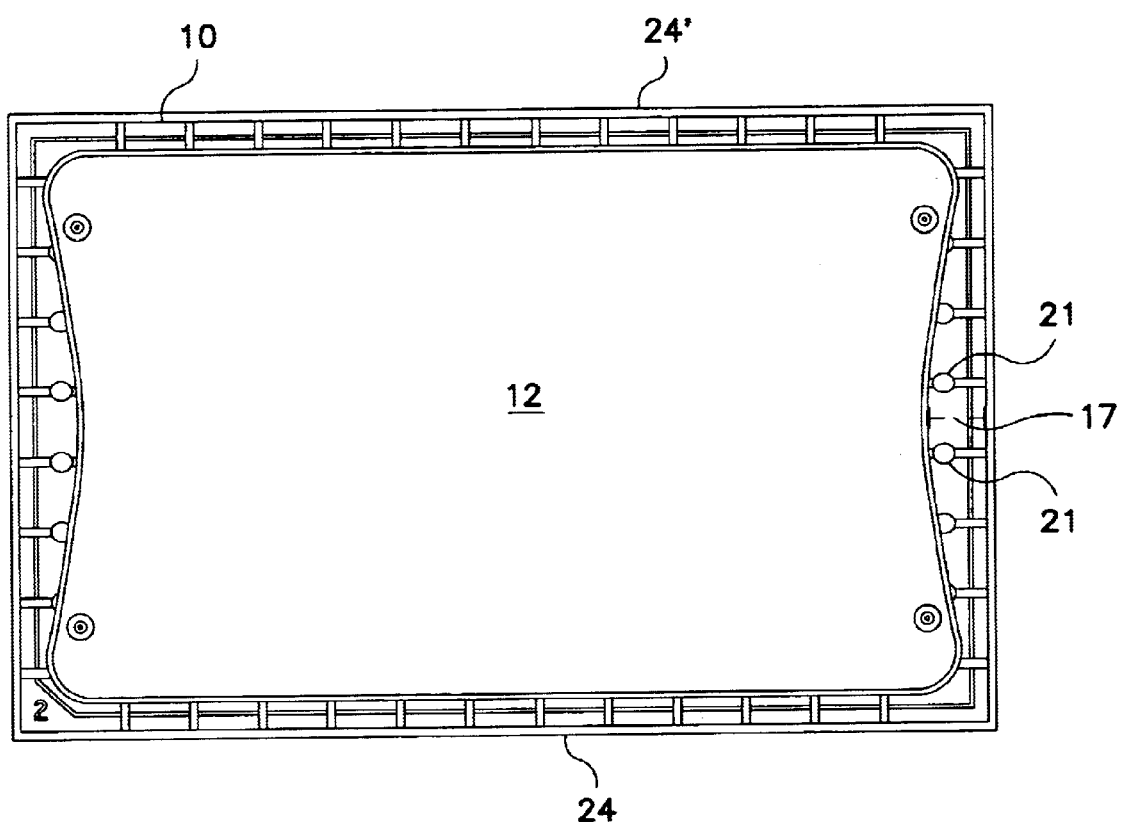
FIG. 3 is a bottom view showing the underside of a multiwell microplate device with the undercover affixed in place in accordance with the present invention.

As shown in FIG. 2, when affixed to the plate 10 to form a unitary assembly, the undercover 12 should cover all of the wells to protect the wells from contamination. The undercover 12 has a length and width smaller than the length and width of the plate 10 so that the undercover 12 is dimensioned to fit inside the skirt 28 of the plate 10. The undercover 12 also is sufficiently thin so that when assembled to plate 10, the skirt 28 of plate 10 extends beyond the undercover 12 as best seen in FIG. 5. This configuration therefore does not alter the compatibility of plate 10 with robotics equipment, and maintains the dimensional standards established in the industry.

Figure 6:
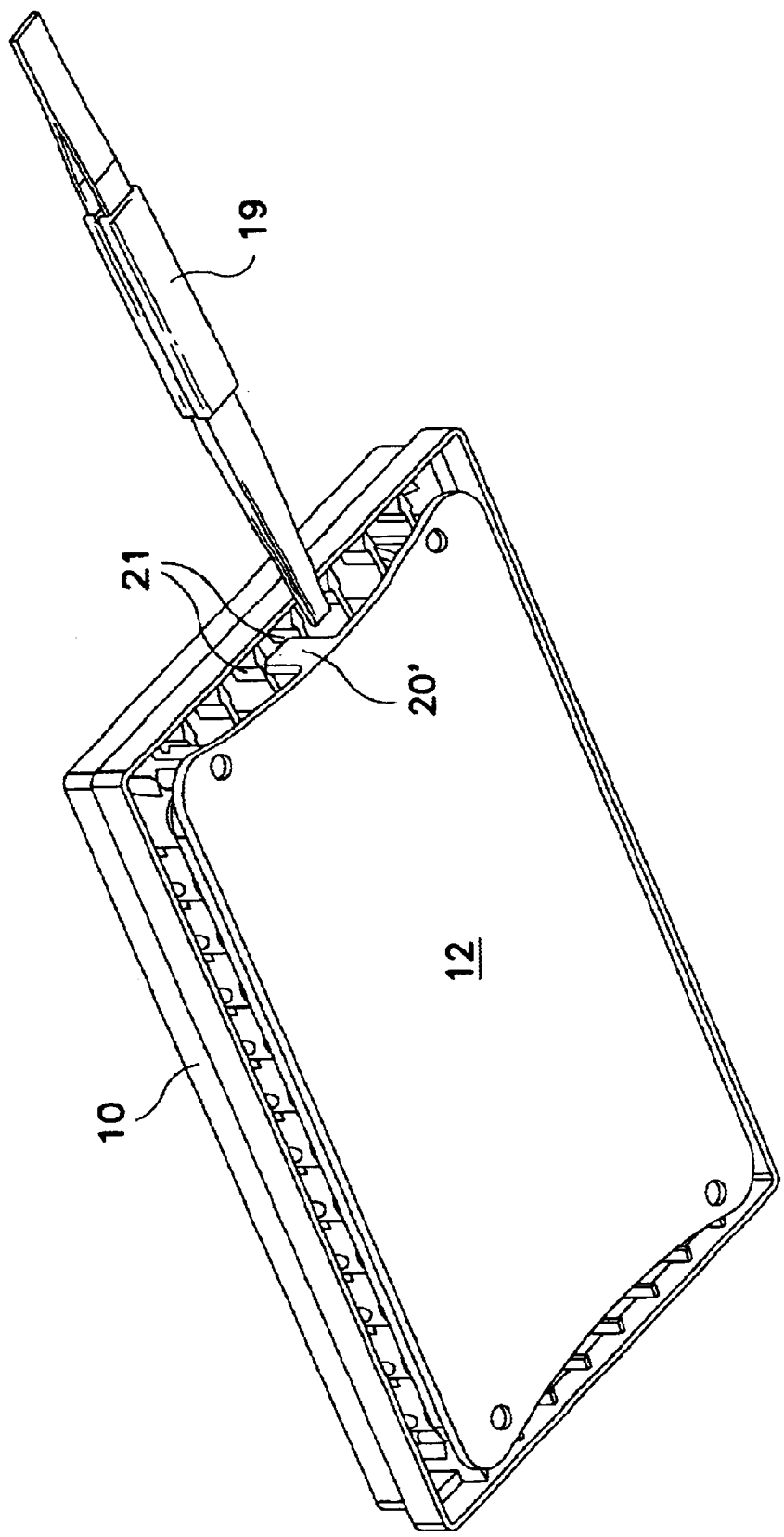
FIG. 6 is a perspective view showing removal of the undercover from the microplate in accordance with the present invention.

Preferably a gap 17 is provided between the edge of the undercover 12 and the edge of the plate 10 to allow for insertion of a finger or tool 19 between the undercover 12 and the plate 10 to pry away the undercover 12 from the plate 10 for removal, as depicted in FIG. 6. Thus, by removing the undercover 12, the operator can gain access to the membrane or support. The gap 17 need not be uniform along the perimeter of the undercover 12.

Figure 4:
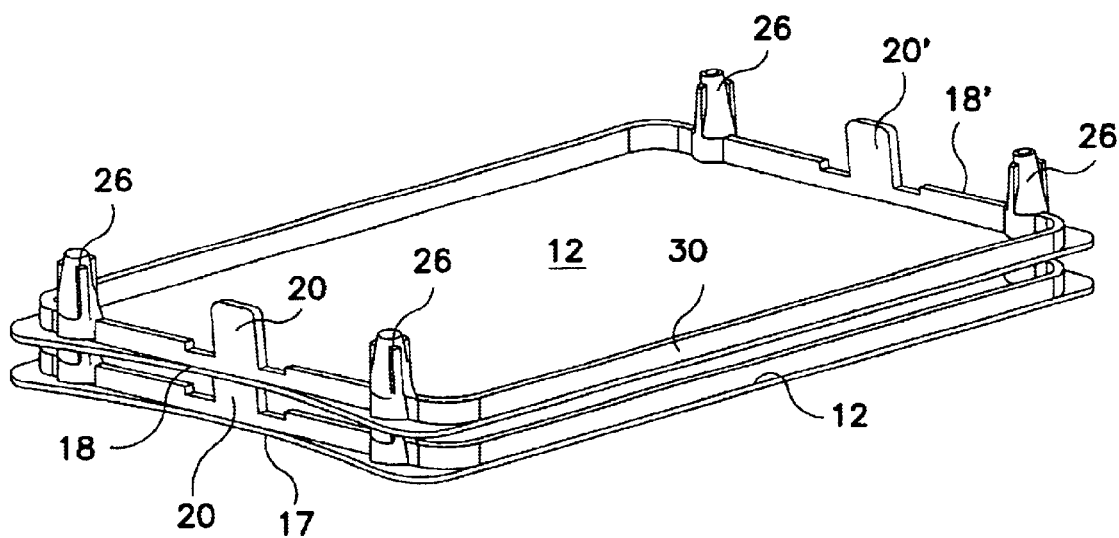
FIG. 4 is a perspective view showing two undercovers stacked in accordance with an embodiment of the present invention.
Figure 7:
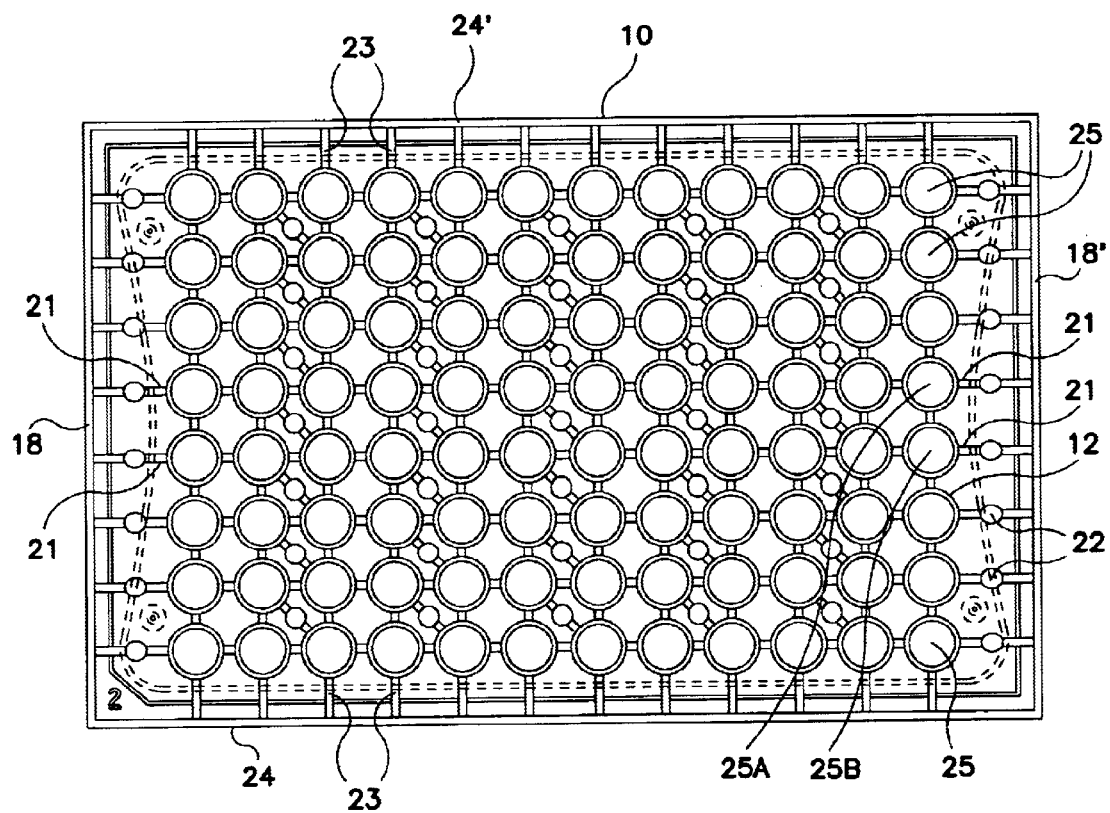
FIG. 7 is a bottom view of the microplate showing the undercover in phantom in accordance with the present invention.

Turning now to FIG. 4, details of the features of the undercover 12 and plate 10 to enable the undercover 12 to be removably affixed to the plate 10 are illustrated. In the embodiment shown, the undercover 12 has a tab 20 extending in a vertical direction relative to the surface of the undercover 12. The tab 20 is preferably centrally located along, adjacent or slightly spaced from the side edge 18 of the undercover 12. The opposite side edge 18' also has a similar tab 20'. The tab 20 is dimensioned to be received between two spaced, preferably parallel ribs 21 (FIG. 7) that extend from each side 18 of the plate 10 to outer walls of respective wells 25 in the underside of plate 10. Each rib 21 can include a cylindrical post 22 that provides structural integrity to the rib 21 and further serves to position the tab 20. The width of the tab 20 is only slightly bigger than the distance between the spaced ribs 21, so that force is necessary to push the tabs into that space and to remove the tabs from that space. As best seen in FIG. 8, the tab 20 thus fits laterally between the two ribs 21 and longitudinally between the outer walls of two consecutive wells 25A, 25B and two consecutive rib posts 22 to assist in locating and securing the undercover 12 to the plate 10. One or more tabs 20 can be used for each side edge 17.

FIG. 4 also shows pins 26 that extend in a vertical direction relative to the surface of the undercover 12. The pins 26 are located at or near opposite corners of each side edge 17 as shown, spaced from the tab 20. The pins 26 also are dimensioned to fit between two adjacent spaced ribs 21 that extend from the side 17 of the plate 10 to outer walls of respective wells 25 in the plate 10, and assist in aligning the undercover 12 with the plate 10. It is not necessary that the pins 25 contact the ribs 21 or the outer walls of the wells 25. The height of the pins 26 is preferably chosen so that the pins 26 contact the underside of the plate 10 to provide a stop to hold the undercover 12 a fixed and minimum distance from the surface of the membrane to prevent the undercover 12 from contacting the membrane when affixed to the plate 10. That is, a clearance 29 (FIGS. 5 and 8) between the surface of the undercover and the surface of the membrane or support 11 is ensured by sizing the pins 26 appropriately based upon the distance each well extends from the underside of the plate 10. A suitable clearance 29 has been found to be between about 0.8–1.0 mm. The pins 26 also add to the structural integrity of the undercover 12, avoiding too much flex, assist in the stackability of the undercovers (FIG. 4) and protect the tabs 20. As seen in FIG. 2, apertures 32 can be formed in the undercover 12 axially aligned with the pins 26, the apertures 32 being configured to receive corresponding pins 26 from another undercover 12 to enhance stackability.

Alternatively or in addition to configuring the pins 26 so as to ensure the clearance 29 between the undercover 12 and the membrane or support 11, the undercover 12 may also include a raised rim 30 at or near the perimeter, as best seen in FIG. 4. The rim 30 may be continuous and encompass the entire perimeter of the undercover 12, or may be discontinuous. The height of the rim 30 is chosen to contact the top surface of the ribs 21 and therefore also act as a stop to prevent the undercover from contacting the membrane or support 11. The top surface of lateral ribs 23 that extend from inwardly towards wells 25 from the longitudinal edges 24, 24' of the undercover 12 also may be contacted and provide a stop to form the clearance 29.

It also is within the scope of the present invention to include one or more vertical pins in the center region of the undercover 12. These additional pins can interlock with the plate and further prevent inadvertent contact between the undercover and the bottom of wells anywhere in the plate, especially the center.

Since the undercover 12 is not fixed to each individual well, unnecessary strain on each well is avoided. Such strain can create membrane bowing that can deleteriously effect imaging.

The clearance between the undercover 12 and the plate skirt of the plate 10 allows for plate stackability, with or without cover 5, as shown in FIG. 5.

In the event it is desirable to have the undercover 12 contact the membrane 11 to support the membrane, the clearance 29 can be eliminated by proper sizing of the rim 30 and pins 26.

What is claimed is:

1. A device comprising:
   a tray having at least one well, said at least one well including a support, said tray having an underside and being dimensioned in the x-y-z directions to be automation compatible; and
   an undercover adapted to be removably affixed to said underside of said tray about said support to form an assembly, said undercover having optical characteristics that allow imaging of said support through said undercover, said undercover, when affixed to said tray, not providing any additional dimension in the x, y or z direction, and positioned at a predetermined distance from and not in contact with said support when affixed to said tray.

2. The device of claim 1, wherein said support is a membrane.

3. The device of claim 1, wherein said undercover is transparent.

4. The device of claim 1, wherein there are a plurality of individual wells and a plurality of individual supports, each individual support being associated with a respective individual well.

5. The device of claim 1, further comprising a removable cover for said tray.

6. A multi-well device comprising:
   a multi-well tray having at plurality of wells, each well including a support, said tray having an underside, said tray having a tray length, a tray width and a tray height; and
   an undercover adapted to be removably affixed to said underside of said tray about said supports to form an assembly having an assembly width that is the same as said tray width, an assembly length that is the same as said tray length, and an assembly height that is the same as said tray height, said undercover positioned at a predetermined distance from and not in contact with said support when fixed to said tray.

7. The multi-well device of claim 6, wherein said support is a membrane.

8. The multi-well device of claim 6, wherein said undercover is transparent.

9. The multi-well device of claim 6, further comprising a cover for said tray.

10. The device of claim 1, wherein said underside of said tray has a plurality of spaced ribs, and wherein said undercover comprises a plurality of vertically extending tabs, each tab being adapted to fit within the space between a respective pair of said ribs to affix said undercover to said tray.

11. The device of claim 1, wherein said underside of said tray has a plurality of spaced ribs, and wherein said undercover has a raised rim about its perimeter that contacts said plurality of ribs upon affixing said undercover to said tray, thereby preventing said undercover from contacting said support when said undercover is affixed to said tray.

12. A device consisting essentially of:
   a tray having at least one well, said at least one well including a support, said tray having an underside; and
   an undercover adapted to be removably affixed to said underside of said tray about said support to form an assembly, said undercover having optical characteristics that allow imaging of said support through said undercover, said undercover positioned at a predetermined distance from and not in contact with said support when affixed to said tray.

* * * * *